US010194926B2

(12) United States Patent
Claes et al.

(10) Patent No.: US 10,194,926 B2
(45) Date of Patent: Feb. 5, 2019

(54) SURGICAL DEVICE FOR PROPER ORIENTATION DURING OSTEOTOMY (71) Applicant: Togema bvba, Herentals (BE)

(72) Inventors: Antoon Claes, Herentals (BE); Gert Vandenbogaert, Nijlen (BE); Marcel De Ceuster, Westerlo (BE)

(73) Assignee: Togema bvba, Herentals (BE)

( * ) Notice: Subject to any disclaimer, the term of this patent is extended or adjusted under 35 U.S.C. 154(b) by 459 days.

(21) Appl. No.: 14/777,437

(22) PCT Filed: Mar. 18, 2014

(86) PCT No.: PCT/EP2014/055458
§ 371 (c)(1),
(2) Date: Sep. 15, 2015

(87) PCT Pub. No.: WO2014/147099
PCT Pub. Date: Sep. 25, 2014

(65) Prior Publication Data
US 2016/0030065 A1   Feb. 4, 2016

(30) Foreign Application Priority Data

Mar. 18, 2013 (BE) .................................. 201300166

(51) Int. Cl.
*A61B 17/58* (2006.01)
*A61B 17/60* (2006.01)
(Continued)

(52) U.S. Cl.
CPC .......... *A61B 17/1728* (2013.01); *A61B 17/02* (2013.01); *A61B 17/151* (2013.01); *A61B 2017/681* (2013.01); *A61B 2090/067* (2016.02)

(58) Field of Classification Search
CPC . A61B 17/151; A61B 17/152; A61B 17/1728; A61B 17/02
(Continued)

(56) References Cited

U.S. PATENT DOCUMENTS

| 8,241,293 | B2 * | 8/2012 | Stone | A61B 17/151 606/87 |
| 2002/0133157 | A1 * | 9/2002 | Sterett | A61B 17/025 606/286 |

(Continued)

FOREIGN PATENT DOCUMENTS

| EP | 2 036 509 | 3/2009 |
| FR | 2 679 126 | 1/1993 |

(Continued)

OTHER PUBLICATIONS

JP2004298259A translation attached.*

Primary Examiner — Si Ming Ku
(74) Attorney, Agent, or Firm — Levy & Grandinetti (57) ABSTRACT A surgical device for osteotomy allows for accurate determination of the angle at which a bone in the human or animal body should be corrected, and for precisely maintaining the angle constant during the entire surgical procedure. The surgical device having on its distal end a circular segment fixed to a distal end of a first blade and further moveably connected to a distal end of a second blade. The distal end of the second blade is allowed to move along the circular segment, wherein the proximal ends of the first and second blade converge at an angle. At least a pair of pin guide openings are provided in parallel for inserting and positioning at least two parallel pins or drill bits. The surgical device provides unique fixed reference means allowing to perform a precise surgery according to predetermined parameters and angles even at the final stages of the operation.

12 Claims, 3 Drawing Sheets (51) Int. Cl.
*A61F 2/00* (2006.01)
*A61B 17/17* (2006.01)
*A61B 17/68* (2006.01)
*A61B 17/02* (2006.01)
*A61B 17/15* (2006.01)
*A61B 90/00* (2016.01)

(58) Field of Classification Search
USPC .................................................. 606/87, 90
See application file for complete search history.

(56) References Cited

U.S. PATENT DOCUMENTS

| | | | |
|---|---|---|---|
| 2002/0165552 A1 | 11/2002 | Duffner | |
| 2005/0273114 A1 | 12/2005 | Novak | |
| 2008/0195099 A1 | 8/2008 | Minas | |
| 2008/0262500 A1 | 10/2008 | Collazo | |
| 2010/0036205 A1* | 2/2010 | Ojima | A61B 17/02 |
| | | | 600/201 |

FOREIGN PATENT DOCUMENTS

| | | | |
|---|---|---|---|
| JP | 2004-298259 | 10/2004 | |
| JP | 2004298259 A * | 10/2004 | A61B 17/15 |

* cited by examiner

FIG 9

SURGICAL DEVICE FOR PROPER ORIENTATION DURING OSTEOTOMY

This Application is the U.S. National Phase of International Application Number PCT/EP2014/055458 filed on Mar. 18, 2014, which claims priority to Belgium Application Number BE201300166 filed on Mar. 18, 2013.

FIELD OF THE INVENTION

The invention relates to a surgical instrument for osteotomy, equipped with two blades, a protractor fixed to one of these blades, 2 or preferably 4, fixed in parallel drill guides for determining the angle at which a bone in the human or animal body should be corrected, and for maintaining said angle during the surgical correction fixing procedure in a precise and reproducible manner.

BACKGROUND OF THE INVENTION

Osteotomy is a surgical operation during which an incision is made in the bone at a specific location in order to correct the alignment of this bone. Osteotomy can be applied to various bones in the human or animal body, but most commonly to the proximal or distal femur, the proximal or distal tibia, the proximal or distal humerus, the forearm and in some cases, the smaller bones like the clavicle, fingers, or toes. The correction is usually carried out on the basis of a predetermined axis. The most common reasons for osteotomic intervention are traumas or congenital abnormalities that affect the joints or bones leading to pain, discomfort, or further complications.

Depending on whether a positive or negative bone inclination adjustment is required, osteotomy can be divided to two realignment procedures. The first type, opening wedge osteotomy, involves creating an incision that is then spread-open using a spreader device to create a broadened wedge-shaped opening which can be filled with a bone substitute. In the second type, closing wedge osteotomy, two incisions are made into the bone to create a wedge-shaped piece that is removed and the gap that is left is closed. Both corrections are then stabilised by fixing the bone ends together with an implant, usually a plate screwed above and below the place where the wedges were formed.

Osteotomy has to be done correctly in the first attempt, given the extensive recovery time and potential complications. The probably most commonly performed osteotomy is done in the vicinity of the knee joint (knee osteotomy). There are currently several devices known in the art serving the exact purpose of aiding knee osteotomy, cf. US20020133157, US2008262500, US2002165552. Several of them make use of hinged spreaders whose opening angle is controlled and optionally measured using a screw-based system cf., EP2036509 or US20050273114. Several devices are equipped with more exact protractors for reading of the angle and may use swinging adjustable pins for stabilising the protractor on the uneven bone surface while estimating the measure of the necessary correction angle, cf. US2008195099, FR2679126. Several of these devices allow a relatively precise calculation of the necessary correction angle during making and spreading the wedge incision, but once such device is removed, the surgeon is left with no exact guideline or points of reference allowing him to control that the pre-determined angle is not being changed during the fixing procedure. Usually, the surgeons have to rely only on 2D X-ray pictures that are being extensively taken during the operation, as none of the currently-available devices provides fixed reference means for guiding the surgeon during fixation of the wedge made in the bone after the angle measuring device has been removed to make way for fixation means. Therefore, there currently exists a need for an economical simple device that would not only uniformly allow the precise calculation of the necessary correction angle, but would also provide means for maintaining this pre-determined angle constant during the fixation of screws and plates, thus also advantageously allowing reduced use and exposure to X-rays.

SUMMARY OF THE INVENTION

The present invention provides a precision surgical device for osteotomy. In a preferred embodiment said device comprises on its distal end a circular segment (D) that is fixed to a distal end of a first blade (A') and is further moveably connected to a distal end of a second blade (A), allowing to move said distal end of the second blade along the circular segment, said device further comprising at least a pair (I and II, or III and IIII) of pin or drill guide openings characterized in that the pin or drill guide openings are provided in parallel for inserting and positioning at least two parallel pins or drill bits (T, T').

In a particular embodiment, the device according to the previous embodiment comprises two pairs (I, II, III, IIII) of said pin guide openings, each pair situated on a different one of the two lateral sides of said device. Said arrangement facilitates application of the device according to the present invention in surgical procedures on bones from both symmetrical sides of human or animal body.

In a particularly advantageous embodiment according to any of the previous embodiments, the proximal ends of the first (A') and second blade (A) converge at an angle whose measure is adjustable through changing the position of the second movable blade (A) along the circular segment.

In a further embodiment in line with the above embodiments, at least one pin guide opening of said at least one pair passes through said circular segment (D), while the remaining pin guide opening from said pair is fixed in either the circular segment (D) or in the first blade (A'), in order to ensure that the parallel relationship of pin guide opening forming a pair is fixed and cannot be changed.

In another embodiment according to any of the previous embodiments, the circular segment (D) of the device according to the invention comprises or is a protractor for reading the angle between the two blades (A', A).

In a particular embodiment, at least one of but preferably both blades (A', A) of the above-described surgical device comprise a chisel-shaped edge (B', B), or simply are chisels. In a specific implementation of the above embodiment, the proximal ends (B', B) of both chisel-shaped blades (A', A) converge forming a double-bladed chisel. In a further practical embodiment in line with the above embodiments, at least one of or preferably both blades (A', A) comprise reference markings, such as incisions or calibrated ruler lines, for determining the depth of the cut (N) into the bone.

According to further implementations of the above embodiments, the surgical device according to the invention comprises means for moving the distal end of the second blade (A) along the circular segment (D), thereby allowing to adjust the angle formed between the converged proximal ends of the two blades (A', A). In a particular embodiment said means is provided as a serrated bolt (G) comprised between the two blades (A', A).

In a more specific embodiment of the above embodiment, wherein said bolt (G) screws directly into a serrated opening in at least one blade, preferably being the first fixed blade (A'), while retaining the ability to rotate freely within a groove (H) provided in the surface of the remaining blade, preferably being the second movable blade (A).

In another specific embodiment, bolt (G) does not screw directly into a blade but screws into a threaded rotatable cylinder (F) positioned in an opening (E) made in at least one lateral side of at least one blade, preferably being the fixed blade (A'), which allows adjusting the angle of the bolt (G) with respect to said blade, while keeping the blot (G) anchored within the second blade either in a fixed point, such as the groove or recess (H), or preferably within a second threaded rotatable cylinder (F) positioned in an opening (E) made in at least one lateral side of the remaining blade, preferably being the adjustable blade (A).

In an embodiment alternative to the embodiments comprising a bolt (G), the means for moving the distal end of the second blade (A) along the circular segment (D) is provided as a worm-shaped screw system with serration on the circular segment (D), either along its convex or concave side.

In a preferred embodiment according to any of the previous embodiments, a surgical device is provided further comprising a separate, preferably fixable and detachable distractor device (R), most preferably either adjustable or comprising at least two open holes (S) and (S') at a distance from each other corresponding to the distance between two parallel pins or drill bits positioned in said at least one pair (I and II; or III and IIII) of the parallel pin guide openings in said surgical device.

In a another aspect, the present invention also provides a separate support correction plate (Q) for the stabilisation of the correction made during osteotomy performed with a surgical device according the present invention, said plate (Q) comprising a plurality of openings wherein at least two openings (P', P) are positioned at a distance from each other corresponding to the distance between the two parallel pins or drill bits positioned in at least one pair of the parallel pin guide openings (I and II; or III and IIII) characterising said surgical device. Of course, in likely embodiments said support plate (Q) preferably further comprises a plurality of additional openings for accommodating screws (U) that fix the support plate (Q) to the bone. In a particular embodiment of the support plate (Q) according to previous embodiments, at least one but preferably more of said additional openings comprise pre-positioned or pre-attached screws (U), said screws preferably comprising sharp ends capable of being drilled into the bone.

In a final aspect, the present invention provides a kit-of-parts comprising the surgical device according to any of the embodiments and preferably also further comprising any one of or any combination of the following:

- any number of, at least one, preferably two, most preferably a plurality of more than two pins or drill bits compatible with the parallel pin guide openings of said surgical device;
- at least one a distractor device (R) meeting the above-described criteria;
- at least one or more of the compatible support plates (Q) as described above;
- any number screws (U) for fixing the support plate (Q) onto the bone.

DESCRIPTION OF THE FIGURES

The figures are provided for schematic purposes and should not be regarded as limiting. For illustrative purposes, dimensions of certain components may be exaggerated or out of scale. Further, the dimensions or the relative dimensions might not always correspond with certain embodiments of the present invention. It should be noted that reference letters and Roman numerals remain constant among different figures and always refer to defined corresponding elements of the device. Finally, it should be noted that reference letters and Roman numerals referred to in the claims may not be construed to limit the claim scope.

REMARKS AND DEFINITIONS

The current invention will be described with respect to particular embodiments and with reference to elements indicated in the figures; however it should be understood that these references are provided for illustrative purposes solely and the present invention is not meant to be limited thereto.

In line with the above, it should be noted that although the following description primarily exemplifies the use of the device of the present invention in "opening wedge osteotomy", it will be apparent to one skilled in the art that said device can also be successfully applied in the "closing wedge osteotomy" procedure that involves cutting and closing the wedge-shaped gap formed in the bone. It should further be remarked that although osteotomy is most commonly performed on the knee joint, the device according to the present invention, can also be scaled and used for measuring and correcting other bones than only femur or tibia.

DETAILED DESCRIPTION OF THE INVENTION

The essential and unique component of this surgical device are the fixed and positioned always in parallel paired pin or drill guides that allow to push and place two perfectly parallel pins in determined locations in the bone, serving as reference points during the entire operation. Thanks to the pin guides, parallel pins precisely mark the opening angle of the wedge that can be controlled with an accuracy to one degree or better, and ensure that the desired angle remains the same throughout the entire operation, importantly also including the stage wherein the fixing support plate is drilled into the bone.

The surgical device of the present invention allows to perform a perfect osteotomy for correcting alignment of bones, in accordance with the pre-calculated correction parameters and in a controlled manner thorough the entire procedure, based on the reference provided by two fixed always-parallel pins.

The disclosed herein design of the surgical apparatus for osteotomy provides to following main advantages:

In contrast to current surgical practices wherein the final correction mostly happens "on sight", the surgical instrument according to the present invention ensures a correct, reproducible way of determining the wedge size beforehand, including also the fixing stage after the removal of the surgical device. In other words, thanks to the marking system of the paired parallel drill guides that guide positioning of 2 parallel reference pins, the opening angle of the wedge incision in the bone remains exactly at the predetermined degrees throughout the entire operation so that the desired axis correction is achieved.

The instrument according to the present invention uses pin guides that allow perfect determination and placing of the reference points for a correct osteotomy, namely:
 1. starting position of the incision,
 2. direction of the incision to be made under a given angle
 3. hinge point where the incision is opened or the angular point of the wedge
 4. proper positioning of drill holes ensuring that the angle of the wedge remains constant, even during filling and fixing.

Thanks to the tight control of these reference points, the use of X-rays is greatly reduced to the necessary minimum, which provides an obvious improvement in timing and safety of the procedure both to the surgeon as well as to the patient.

In a preferred embodiment, the surgical device of the invention comprises on its distal end a circular or arched segment (D) that is firmly fixed to a distal end of a one blade (A'), further referred to as the first blade or the fixed blade (A'), and that is also further moveably connected to a distal end of another blade (A), further referred to as the second blade or the adjustable blade, in such way that allows to move said distal end of the second blade along the circular segment. In this embodiment, the fixed part of the device defined by the circular segment (D) and the fixed blade (A') comprises at least one pair composed of two perfectly-parallel openings or tunnels (I, II), further referred to as pin (or drill) guides, that are capable of accommodating and maintaining in a defined spacial alignment parallel to one another surgical pins or drill bits (T', T), wherein at least one of these two parallel pin guides (II) is positioned within the circular segment (D). Such arrangement allows to move or slide the second blade (A) along the circular segment (D) with respect to the first fixed blade (A') within a defined and fixed reference system provided by 2 perfectly parallel pins when inserted into the pair of fixed parallel pin guides. This results in provision of fixed reference plane in which the position, for example expressed in degrees, of the second movable blade (A) can be determined with respect to pins and the fixed blade (A').

In a preferred embodiment the fixed blade (A') and the second moveable blade (A) converge with their proximal ends or edges at an angle, wherein the size of the angle can be estimated or read on from the position of the distal end of the movable blade (A) within the circular segment (D) that can preferably serve as a protractor.

In a further preferred embodiment, the device according to the previous embodiment comprises two pairs (I and II; and III and III) of pin or drill guide openings, provided in parallel (at least within one pair) for inserting and positioning at least two parallel pins or drill bits (T, T'). As used herein "positioning" refers to the ability to move said pins or drill bits within the guide openings while maintaining their parallel position with respect to one another, i.e. ensuring that the ends of said pins used as reference points will never converge.

According to an advantageous embodiment of the present invention, the openings or tunnels of the pin guides are suitable for removing the device while leaving the parallel pins attached to their target, such as bone or joint surface.

In a preferred embodiment, the circular segment (D) is or comprises protractor for reading the angle between the two blades (A' and A). Like this, when the angle between the two blades (A' and A) is changed due to the movement of the distal end of the second blade (A) along the arc of the protractor (D), the angle can be read by a surgeon from the position of the pointer marked or etched on the distal end of the second blade (A) and pointing or aligning with the scale provided on the protractor (D). In an alternative embodiment, the angle between the two blades (A', A) can be measured and/or read with an electronic device, either directly coupled to the surgical device according to the invention or recording it.

In a preferred embodiment, any one of the two (A' or A) but preferably both blades (A' and A) comprise a chisel-shaped proximal edge (B', B), or simply are chisels.

In one desired embodiment, the proximal ends (B', B) of both chisel-shaped blades (A', A) converge forming a double-bladed chisel, which is advantageous for the reason it minimises the risk of causing the occurrence of fracture lines on the joint surface or the lateral cortex during the wedge-opening procedure in the bone. In a preferred embodiment, the device of the present invention comprises double-blade chisel and is also equipped with a protractor.

Therefore, in an advantageous embodiment, the present invention provides a surgical device for osteotomy comprising a protractor on its distal end, said protractor comprising an arched protractor body defined by the circular segment, said protractor body being fixed to a distal end of a first chisel (A'), and said protractor body being further connected to a distal end of a second chisel (A) in any manner allowing to move said distal end of the second chisel (A) along the arched protractor body, wherein both blades are inclined towards one another and converge with their proximal-end profiles thus defining a vertex of an angle formed between said two chisels (A' and A), or more exactly between the two cutting edges (B' and B) of said chisels, said angle's measure being adjustable by moving the distal end of the second chisel (A) along the arched protractor body, and wherein said device is characterised in that two pairs of parallel pin guide openings are provided to allow guiding of at least two parallel pins or drill bits along the sides of the device, wherein at least one guide opening in each pair passes through the arched protractor body, while the second guide opening of each pair is fixed in either the arched protractor body or in the first fixed chisel (A').

In a further advantageous embodiment of the present invention, at least one but preferably both of the blades (A', A) comprise reference markings, such as incisions or calibrated ruler lines allowing to determine the depth of the cut (N) into the bone.

In a further embodiment, the surgical device can also be equipped with a distractor, a specific instrument allowing to temporarily stabilise the pins marking the medial opening until the wedge is filled with bone substitute or bone grafts and until the osteotomy plate is fixed.

In a preferred embodiment, the surgical device according to the invention is provided with a highly compatible with the surgical device but separate distractor device extension, said distractor device (R) preferably being easily fixable and detachable to the device. In preferred embodiments, said distractor is either adjustable or comprises at least two open holes (S) and (S') at a distance from each other corresponding to the distance between two parallel pins or drill bits positioned in at least one pair (I and II; or III and IIII) of the parallel pin or drill guide openings in the surgical device according to the invention In another but very important aspect of the present invention, support plates (Q) for fixing the bone correction are provided such that they are compatible with accommodating or being slid upon the parallel pins introduced by the surgical device according the invention. In a particular embodiment, said support plates (Q) would be provided in a form comprising a plurality of openings comprising at least two openings (P', P) at a distance from each other corresponding to the distance between two parallel pins bits positioned in at least one pair (I and II; or III and IIII) of the parallel pin guides of the surgical device according to any of the embodiments of the present invention. In a likely embodiment, said compatible support plate (Q) would also further comprise a plurality of additional openings for accommodating screws (U) for fixing said plate (Q) onto the bone. In a particular embodiment, said plate could also be provided comprising a plurality of fixation screws (U) pre-positioned in said additional openings, said screws preferably comprising sharp ends capable of being drilled into the bone.

In a yet another aspect of the present invention, a kit of parts would be provided comprising the surgical device according to any of the described embodiments.

Advantageously, said kit of parts could also be provided further comprising some or any of the following:
  pins or drill bits compatible with the parallel pin or drill guide openings of said surgical device;
  the separate extension compatible distractor device (R) as described above;
  any number of the compatible support plates (Q) as described above;
  plurality of screws (U) for fixing the support plate (Q) onto the bone; etc.

Examples of the Device According to the Invention

Figure 1:
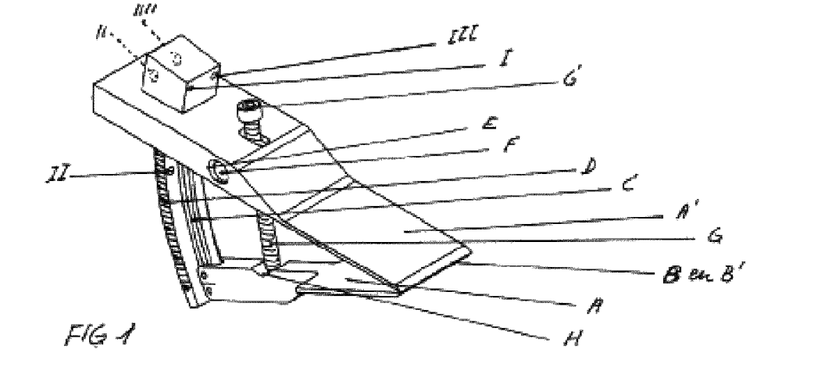
FIG. 1 schematically illustrates the surgical device according to one embodiment of the invention, as viewed along the front edge, obliquely from above.
Figure 2:
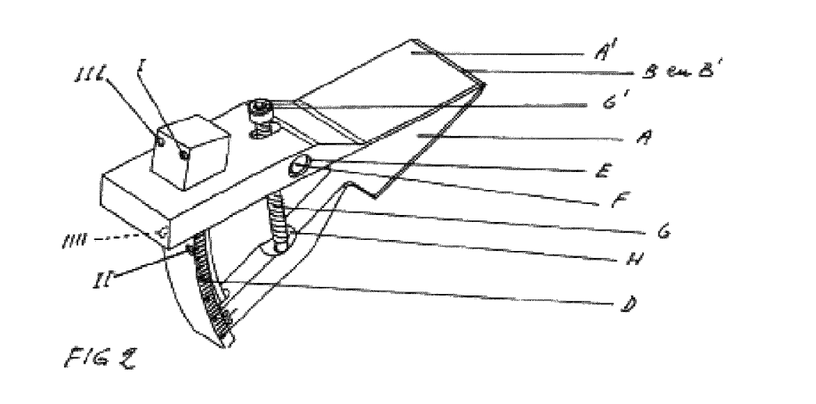
FIG. 2 schematically illustrates the surgical device according to one embodiment of the invention, as viewed along the back edge, obliquely from above.
Figure 3:
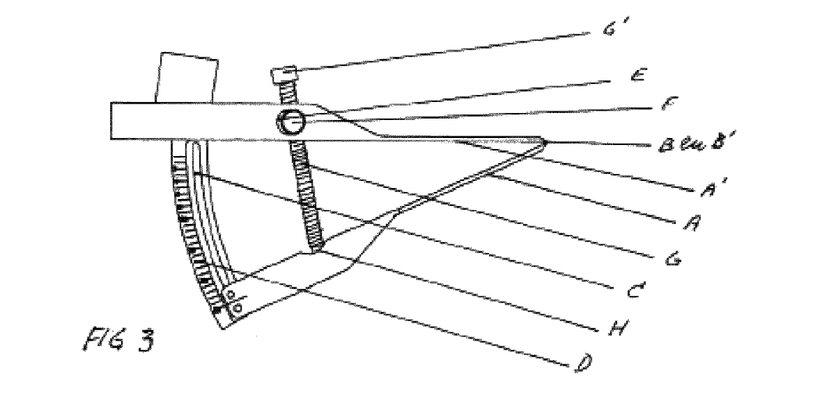
FIG. 3 schematically illustrates the surgical device according to one embodiment of the invention, tilted in such way to show the groove or arched slot (H) in the adjustable bottom blade (A) and the degrees or scale of the protractor comprised in the arched circular segment (D) on which the bottom blade (A) can be adjusted.
Figure 4:
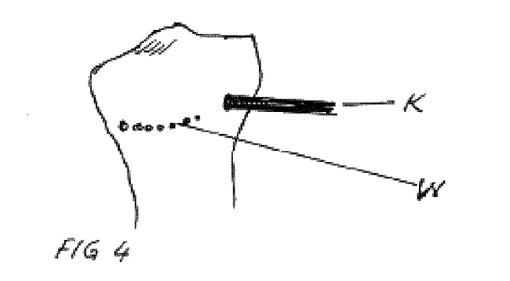
FIG. 4 schematically illustrates determination of a pivot point via pin (K) and incision (W) on a bone (drawn for illustrative purposes) at the beginning of osteotomy.
Figure 7:
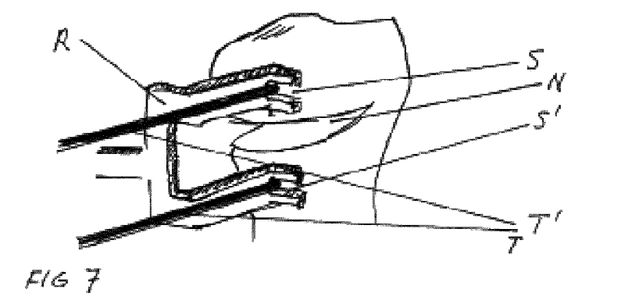
FIG. 7 schematically illustrates the distractor (R) that is placed on the previously positioned parallel pins (T) and (T').

In one example illustrated in the figures, the invention provides a surgical device that comprises 4 parallel drill guides (I), (II), (III) and (IIII); a composite planetary chisel comprising two chisels (A) and (A'); a protractor (D), as illustrated in FIGS. 1, 2 and 3; and a distractor, as illustrated in FIG. 7.

Figure 9:
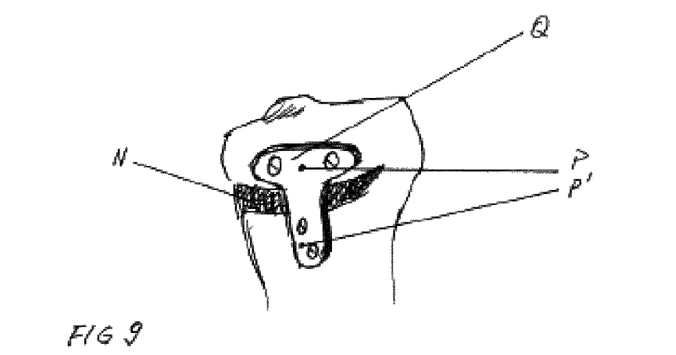
FIG. 9 schematically illustrates the final support plate (Q) screwed above and below the open flared and filled incision (N), as final result.

The 4 parallel drill guides (I), (II), (III) and (IIII) are the key specific components of the surgical device according the provided herein practical example of the present invention. The fixed parallel arrangement of the pin guides in the exemplary embodiment of the device of the invention ensure through a proper guidance of 2 pins with a somewhat smaller diameter, the device provides long-term and reproducible reference points throughout the entire operation. Importantly, this also applies to the operation stages after the surgical device is removed from the wedge-shaped incision and the end plate (Q) is fastened, as indicated in FIG. 9.

The planetary chisel (A) and (A'), shown over FIGS. 1-6, comprises 2 cutting surfaces (B) and (B') which touch each other providing gripping of one chisel onto the other. The 2 chisels together form a cutting edge which provides greater accuracy than an arrangement of 2 chisels with a notch, wherein one chisel rests in the notch of the other chisel. The widths of chisels (A) and (A') are selected in such to match with their intended use during operation, namely they are adapted according to dimensions of the target bone to be operated, for example the leg diameter of the human or animal body. The width of chisel (A) and (A') is preferably much wider than of chisels used in the state of the art, which has the advantage that the wider chisels do not push into a bone weakened due to osteoporosis. Also, using narrow chisels, as provided in most devices known in the state of the art, to create and opening in a broad bone, the opening may be uneven or tilted, may collapse on the edges, leading to correction errors. The cutting surfaces (B) and (B') thus remain against each other at all times, but can be hinged, or change the angle between them. Usually, there is no need for including dimensional scale for the indication of the depth of chisel entry, because according the exemplary embodiment as provided herein, chisels are inserted into a pre-determined point. In the provided herein detailed example of one embodiment of the invention, the distal end of the adjustable chisel (A) is connected or hinged to an arched slot (C) following the curvature of circular segment or the protractor (D). This curvature of both the slot (C) and the protractor (D) preferably describe a segment of a circle with constant radius, as shown in FIG. 3. The slot (C) is preferably a part of the protractor (D), which steadfastly fixed to the back side of the immovable chisel (A'). In the provided herein example, in the side of chisel (A') there is an opening (E), where a threaded cylinder-shaped system (F) can move loosely, allowing to change change the angle of the bolt (G) that is compatibly serrated or threaded with the threaded cylinder (F). Depending on the angle of the chisels (A) with regard to (A'), thanks to this rotatable cylindrical system (F), the end of the bolt (G) can always remain in a groove or a recess (H) formed in the internal surface of the movable chisel (A).

In general there are known in the art multiple different means to provide and control the movement of the distal end of the movable chisel (A) along the protractor (D) and thereby allowing to adjust the angle formed between the converged proximal ends of the two chisel-formed blades (A', A).

The above described serrated bolt (G) comprised between the two chisels (A', A) is one of them. An alternative example could be a moving means provided as a worm-shaped screw system with serration on the arc or the circular segment (D), either along its convex or concave side. In the latter system no bolt (G) is used, but that the angle between the chisels (A) and (A') of the surgical device is changed via relative movement of gear teeth on the arc.

In general, blot (G)-based solutions are more commonly used in the art. As described above, possible embodiments of the device may comprise a bolt (G) that screws directly into at least one chisel or a differently-shaped blade, preferably being the fixed blade (A'), while sliding freely within a groove or other a recess (H) formed in the surface of the remaining blade, preferably being the moving blade (A). In such solution, one end of the bolt (G) screws directly into a serrated opening in the fixed chisel (A') while its opposite end can move freely along the inner surface of the chisel (A) or an elongated groove (H) formed in said surface. In other words, in this simple solution there is no need for opening (E) or cylinder (F). However, although more complicated, the exemplary solution based on the threaded cylinder (F) is particularly advantageous for providing smoother adjustment of the bolt (G) position with respect to movable chisel (A) sides during the adjustment of the angle formed between the blades (A' and A). Briefly and for illustration purposes, bolt (G) may preferably screw into a threaded rotatable cylinder (F) positioned in an opening (E) made in at least one lateral side of at least one blade, preferably being the fixed chisel (A'). This will allows adjusting of the bolt (G) angle with respect to said blade while keeping it on the opposite end anchored within the second blade either in a fixed point, such as a groove or recess (H), or preferably in a second threaded rotatable cylinder (F) positioned in an opening (E) made in at least one lateral side of the remaining blade, preferably being the second movable chisel (A). The latter solution allows to achieve the broadest ranges of the angle comprised between the two chisels.

The screwing of the bolt (G) can be performed manually, or with an aid of a tool such as a screwdriver, electric screwdriver/drill. To facilitate this, one side of the blot (G) may comprise a slot for accommodating screwdriver end, or advantageously be comprise a bolt head (G') for better gripping by hand or joining with a tool. Known in the art bolt heads (G') applicable with the present invention, for example include:

hexagonal bolt head (G') compatible with Allen key system;

bolt head (G') equipped with one or more slots, preferably with a star-shaped, compatible with a screwdriver or star screwdriver, respectively;

bolt head (G') provided with a smooth or serrated button or turnable extension, capable of being turned without any external screwing device.

Figure 5:
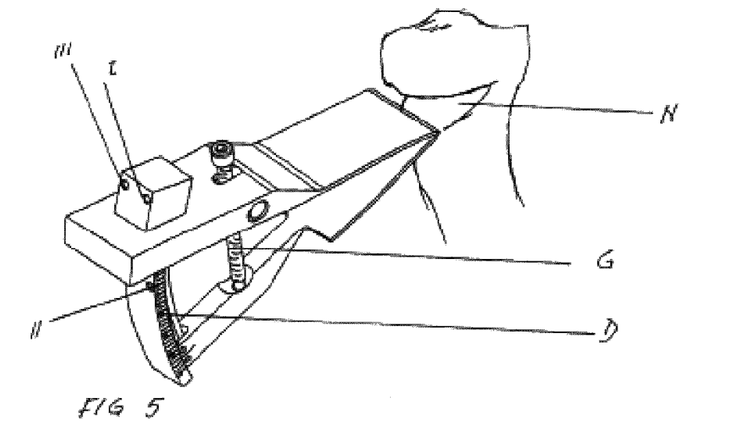
FIG. 5 schematically illustrates flaring of the incision to a wedge-shaped opening (N) in the bone, to be performed with the surgical device according to the invention.

At the start of osteotomy, the first step usually involves determination of a hinge point and the depth of the cut. This is done by for example through applying a perpendicular pin (K) at approximately the lateral cortex of an exemplary schematic fibula, illustrated in FIG. 4. After this pin (K) is placed, an incision preferably perpendicular to the pin (K) is prepared by drilling parallel holes (W) from the medial cortex up to the above mentioned pin (K). These parallel holes (W) ensure that a chisel or an oscillating saw is guided to this pin (K) while cutting into the bone. After the incision (N) is made with a chisel, other blade, or an oscillating saw, the above mentioned pin (K) is removed. At this point, using the surgical device according to present invention, the incision (N) can be pulled open to a wedge-shaped open incision (N), as illustrated in FIG. 5, by rotating the bolt (G) until the desired correction angle is obtained, as measured on the protractor (D). In the presented example of the surgical device according to the invention, 4 round parallel openings (I, II, III and IIII) are provided on the back side of the protractor (D), pointing in the same direction as the chisels (A) and (A'), as illustrated in FIG. 2 where the opening (III) is indicated with a dotted line. These 4 openings serve as drill guides that will determine the correct orientation of the holes that are made in the bone, and these holes will remain the reference points throughout the entire operation. These preferably parallel drill guide openings have a certain angle with respect to upper chisel (A) and ensure that the holes under this specific angle can be drilled in the lateral cortex of the bone. There are 2 paired openings (III and IIII) provided on the left side of the back of the protractor (D) and 2 paired openings (I and II) on the right hand side of the back of the protractor (D), as illustrated in FIG. 2. These openings on the left (III and IIII) and on the right (I and II) ensure that the operation can be performed on either the left bone or on the right bone, respectively. The parallel openings on the left (III and IIII) and on the right (I and II) are at a certain distance from each other. This well-defined distance is the same as the distance of the holes (S) and (S') in the distractor (R) illustrated in FIG. 7. Thanks to this, the wedge or flared incision (N) is kept open with a compatible distractor device (R) after the surgical example of the invention is removed. Furthermore, two openings separated by the same distance are also provided in the final mounting plate (Q) as illustrated in FIG. 9, which allows to slide the plate on the parallel pins held by the distractor and by such maintain the stable angle of the correction upon fixing.

We now discuss the openings (I) and (II) which are used for one bone, while (III) and (IIII) are used for the other bone.

Figure 6:
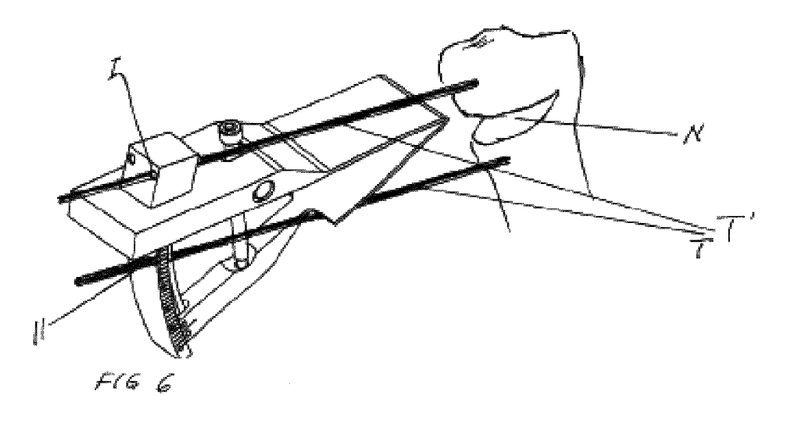
FIG. 6 schematically illustrates how the parallel pins (T) and (T') are entered into the bone through the parallel pin guides above (I) and below (II) the open flared incision (N).

As mentioned above, the openings (I) and (II) are parallel to each other. These parallel openings (I) and (II) serve as guides for the insertion of two parallel (T) and (T'), as illustrated in FIG. 6, below and above the wedge-shaped incision in the bone (N). These parallel pins (T) and (T') will then be immobilised by distractor while applying the final plate (Q) comprising the corresponding holes (P) and (P'), as illustrated in FIG. 9. These holes (P) and (P') of the plate (Q), as illustrated in FIG. 9, are thus at the same distance as the holes (I) and (II) on the back of the protractor (D) illustrated in FIG. 5 and FIG. 6, and at the same distance as the laterally open openings (S) and (S') in the distractor device (R), illustrated in FIG. 7.

Consequently, the 2 pins (T) and (T') can be inserted above and below the bone incision (N), as shown in FIG. 6. Since the drill guides (I) and (II) are parallel, the pins (T) and (T') are also parallel in the bone, and the surgical device, as indicated in FIG. 6, can also be retraced in the flared state from the wedge formed incision (N).

Prior to fully removing the surgical device, according to the exemplary embodiment of the invention, the distractor device (R) is preferably placed on the pins (T) and (T') as indicated in FIG. 7. This is preferably done laterally, as the openings (S) and (S') along the side are open. In this way the cut is kept open at the exact predetermined angle, which results in a precise and controlled surgical intervention. Once the exemplary embodiment of the surgical device of the invention is removed, the incision can be filled with bone substitute or bone graft (V).

Figure 8:
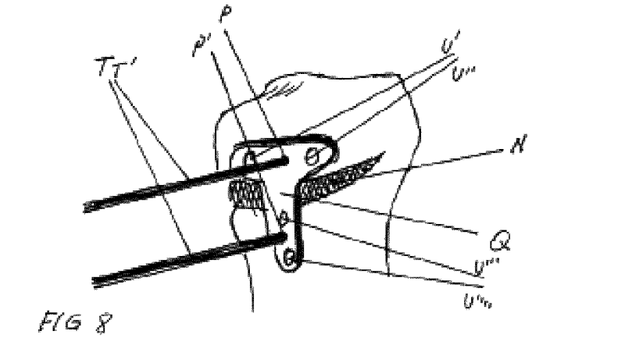
FIG. 8 schematically illustrates the final support plate (Q) that is slid over the pins (T) and (T') that provide guidelines ensuring the previously made wedge-angle remains constant.

Then, after the bone substitute is placed (V), the support plate (Q), with corresponding pin holes (P) and (P'), as indicated in FIG. 8, is moved over the parallel pins (T) and (T') to the medial cortex, while at the same time, the distractor device (R) is removed laterally.

Finally, the support plate (Q) is fixed by fastening the screws (U'), (U"), (U"') and (U"") above and below the incision, illustrated in FIG. 9. Finally the parallel pins (T) and (T') can be removed and osteotomy is concluded with precision in a correct manner according to pre-determined parameters.

Of course, the above-described exemplary device fulfilling the criteria of the present invention or the surgical procedure using said device, by no means should be regarded as limiting as they exemplified only one possible solution according to which said device can be manufactured. Alternative embodiments can easily be envisaged by a skilled person, for example a device wherein no bolt (G) is used, and the angle between the chisels (A) and (A') of the surgical device is adjusted via a worm-shaped screw with gear teeth on the arch. According to another embodiment, the parallel pin guides can be mounted laterally to the sides of the fixed part of the device, etc. Therefore, while different possible embodiments described herein provide some characteristics that may not be included embodiments, it should readily be acknowledged by a skilled person that combinations of said characteristics are included in the scope of the invention, and simply provide just more possible embodiment of the invention.

The invention claimed is:

1. A surgical device for osteotomy comprising;
on its distal end a circular segment fixed to a distal end of a first blade and further moveably connected to a distal end of a second blade, allowing to move said distal end of the second blade along the circular segment, wherein the proximal ends of the first and second blade converge at an angle,
said device further comprising at least a pair of pin guide openings wherein the pin guide openings are provided in parallel for inserting and positioning at least two parallel pins or drill bits, and
an at least one pin guide opening in said at least one pair passes through said circular segment, while the remaining pin guide opening from said pair is fixed in either the circular segment or in the first blade.

2. The surgical device according to claim 1, wherein said circular segment comprises a protractor for reading the angle between the two blades.

3. The surgical device according to claim 1, wherein at least one of or both of the blades comprise chisel-shaped edge.

4. The surgical device according to claim 3, wherein the proximal ends of both chisel-shaped blades converge forming a double-bladed chisel.

5. The surgical device according to claim 1, whereby at least one of or both of the blades comprise reference markings, such as incisions or calibrated ruler lines, for determining the depth of the cut into the bone.

6. The surgical device according to claim 1 further comprising means for moving the distal end of the second blade along the circular segment, thereby allowing to adjust the angle formed between the converged proximal ends of the two blades.

7. The surgical device according to claim 6, wherein said means is provided as a serrated bolt comprised between the two blades.

8. The surgical device according to claim 7, wherein said bolt screws directly into at least one blade, while rotating freely within a groove provided in the surface of the remaining blade.

9. The surgical device according to claim 7, wherein said bolt screws into a threaded rotatable cylinder positioned in an opening made in at least one lateral side of at least one blade, which allows adjusting the angle of the bolt with respect to said blade while anchored within the second blade either in a fixed point, such as groove, or in a second threaded rotatable cylinder positioned in an opening made in at least one lateral side of the remaining blade.

10. The surgical device according to claim 6, wherein said means is provided as a worm-shaped screw system with serration on the circular segment, either along its convex or concave side.

11. The surgical device according to claim 1 further comprising a separate fixable and detachable distractor device, either adjustable or comprising at least two open holes at a distance from each other corresponding to the distance between two parallel pins or drill bits positioned in said at least one pair of the parallel pin guide openings in said surgical device.

12. A kit-of-parts comprising the surgical device according to claim 1 further comprising any one of or any combination of the following:
any number of pins compatible with the parallel pin guide openings of said surgical device;
any number of drill bits compatible with the parallel pin guide openings of said surgical device;
at least one distractor device either adjustable or comprising at least two open holes at a distance from each other corresponding to the distance between two parallel pins or drill bits positioned in said at least one pair of the parallel pin guide openings in said surgical device;
any number of support plates comprising a plurality of openings comprising at least two openings at a distance from each other corresponding to the distance between two parallel pins or drill bits positioned in said at least one pair of the parallel pin guide openings of the surgical device, said support plate further comprising a plurality of additional openings for accommodating screws that fix the support plate to the bone and comprising a plurality of said screws pre-positioned in said additional openings;
any number screws for fixing the support plate onto the bone.

* * * * *